United States Patent [19]

Stjepanovic et al.

[11] 4,322,410

[45] Mar. 30, 1982

[54] P-ACETAMINOPHENYL PHOSPHATE SALTS AS ANALGESICS AND ANTIPYRETICS

[75] Inventors: Milorad Stjepanovic, Chatou; Michèle Moreau, née Huguet, Paris, both of France; Jacques Dugniolle, 8 rue du Centre, Neuilly sur Seine, France, 92200

[73] Assignee: Jacques Dugniolle, Neuilly sur Seine, France

[21] Appl. No.: 100,005

[22] Filed: Dec. 4, 1979

[30] Foreign Application Priority Data

Dec. 15, 1978 [FR] France ............... 78 35429

[51] Int. Cl.³ .................. A61K 31/71; C07F 9/09
[52] U.S. Cl. .................... 424/180; 260/924; 260/944; 424/211; 536/27
[58] Field of Search .......... 260/944, 924; 424/211, 424/180, 24; 536/27, 77

[56] References Cited

U.S. PATENT DOCUMENTS 2,023,551 12/1935 Rosenzweig ............ 260/924
3,032,555 5/1962 Oxley et al. ............ 260/944
3,107,262 10/1963 Rochen ............ 260/924

FOREIGN PATENT DOCUMENTS 254421 8/1911 Fed. Rep. of Germany .

OTHER PUBLICATIONS

Buehler, et al., "Survey of Organc Syntheses", Wiley-Interscience, New York, (1974), pp. 413-414.
Bollinger, "Chem. Abs.", vol. 43 (1949), p. 173 g & h.
Houben-Weyl, vol. 12, No. 7, p. 161.
Galstakhoua, et al., "Chem. Abstracts", vol. 81 (1979). 25304n.
Bellstein, (1951), p. 494.

*Primary Examiner*—Anton H. Sutto
*Attorney, Agent, or Firm*—Irvin A. Lavine

[57] ABSTRACT

The invention relates, as an analgesic and antipyretic medicine, to a paracetamol derivative highly soluble in water, namely the p-acetaminophenyl phosphate in the form of its salts, with pharmaceutically suitable mineral and organic bases, and in particular sodium, glycine, lysine and adenosine salts.

The invention further relates to a process for the preparation of p-acetaminophenyl phosphate from the p-nitrophenol phosphoric ester.

10 Claims, No Drawings

P-ACETAMINOPHENYL PHOSPHATE SALTS AS ANALGESICS AND ANTIPYRETICS

The paracetamol or N-acetyl-p-aminophenol is highly rated amongst currently used analgesic and antipyretic medicines.

The paracetamol, having a low rate of solubility in water (about 1.3 g per 100 ml), is normally used orally, in tablet or suspension form, which requires the use of solubilizing solvents such as glycerol, glycols in variable proportions, as well as other adjuvants, presenting certain drawbacks as far as the taste or the viscosity of the product is concerned.

The present invention relates to a new paracetamol derivative which is especially soluble in water, and permits to obtain high concentrations of the active principle, without adjuvants being added, and therefore which can be used easily for parenteral administrations, by intramuscular or intravenous route, as well as for an oral administration, where it needs to be placed in solution in water such as, for example, when used in sachet form.

Pharmacological tests conducted in animals with the product according to the invention have revealed analgesic and antipyretic properties that are quite comparable to those of the paracetamol, thereby allowing its use on humans for treating pains of various origins, whether or not these pains are associated to hyperthermia. Said product may be used by oral or parenteral route at doses varying between 0.5 g and 6 g every 24 hours depending on the administration route selected and on the sensibility of the patient.

The new paracetamol derivative according to the invention is the paracetamol phosphoric ester or the p-acetaminophenyl phosphate of formula:

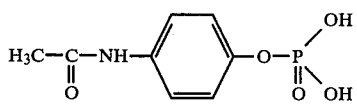  (I)

used in the form of its salts with suitable mineral or organic bases for a therapeutical use. The preferred salts according to the invention, disodium salt, salts of aminoacids such as glycine, lysine and adenosine salts.

The invention further relates to the process for preparing the p-acetaminophenyl phosphate obtained from p-nitrophenol phosphoric ester in disodium form, which is reduced with a carbon-palladium catalyst at 5% in order to obtain p-aminophenyl phosphate thereafter acetylated in the presence of acetic anhydride. The modes of preparation are indicated in the following examples:

EXAMPLE 1

First step: Preparation of disodium salt of p-aminophenyl phosphate.

25 g of disodium salt of hexahydrated p-nitrophenyl monophosphate are hydrogenated under atmospheric pressure and at room temperature, in 2 l of ethanol at 50% in the presence of 4 g of palladium carbon catalyst at 5%. Dry-evaporation takes place after removal of the catalyst.

The residue is dissolved in absolute ethanol, and then drained and dried at 60° C. for 4 hours. About 15 g of anhydrous product is obtained.

Second step: Preparation of disodium salt of p-acetaminophenyl phosphate.

In a balloon flask containing 200 ml of acetic anhydride, are added gradually 15 g of the disodium salt of p-aminophenyl phosphate. After stirring for 30 mins., 500 ml of ether are added and the stirring is resumed for 30 mins.

250 ml of ketone and 10 ml of water are added to the precipitate and the mixture is stirred again for 15 mins. Said mixture is drained, washed with twice 450 ml of ketone and then dissolved in 150 ml of ethanol.

The solution is left to stand for 12 hours at room temperature, then it is drained, washed with twice 15 ml of ethanol and dried at 60° C. About 13 g of the raw product is obtained, which is dissolved again in 60 ml of water, after which 1.5 g of decolorant black are added. After filtration, the filtrate is diluted in 500 ml of ketone. The disodium salt of N-acetyl-p-aminophenol phosphate is stirred and drained. After several washes in ketone, the product is dried for 2 hours at 60° C., and then for a whole night at 105° C.

About 7.5 g of disodium salt are obtained in colorless crystal forms, the melting point of which is greater than 265° C.

This product is readily soluble in water at the rate of 50 g for 100 ml at room temperature. The solution is perfectly stable and has a neutral pH.

EXAMPLE 2

The p-acetaminophenyl phosphate is prepared by acidification of an aqueous solution of its disodium salt. The acid-ester prepared this way is in colorless crystals form containing one mol of water per mol of product [M.P.=135° C. (dehydration); 205° C. (anhydrous product)].

The glycine salt of p-acetaminophenyl phosphate is prepared by dissolving equimolecular quantities of glycine and of the acid-ester in water at 25° C., followed by precipitation with ketone and recrystallization in ethanol at 85%. Said salt is in colorless crystals form (M.P. 195° C.).

The lysine salt is prepared in the same way, using ethanol instead of ketone for the precipitation. Colorless crystals M.P. 179°–181° C. (Büchi capillary tube).

The pharmacological tests have revealed the analgesic and antipyretic properties of the p-acetaminophenyl phosphate and of its salts, which properties are quite comparable to those of the paracetamol; they have also revealed a toxicity of the same order.

DISODIUM SALT OF P-ACETAMINOPHENYL PHOSPHATE (1) Acute toxicity

The DL$_{50}$ determined orally in mice is of the order of 1,200 mg/kg, which is equivalent to that of the paracetamol on an equimolecular basis.

(2) Analgesic activity

This is determined with the Koster R. et al. test (Fed. Proc., 1959, 18, 412) which consists in injecting 0.5 ml, intraperitoneally, of acetic acid at 0.5% to a mouse and in counting the number of contorsions during the following 10 minutes; the analgesic effect of the product according to the invention administered orally one hour before the test is revealed by a % reduction of the number of contorsions compared with the controls.

| | Dose mg/kg | Activity |
|---|---|---|
| Product of the invention (Disodium salt) | 275 (= 1 millimole) | 54% |
| Paracetamol | 150 (= 1 millimole) | 52% |

(3) Antipyretic Activity

This is determined with the Winder et al. test (J. Pharm. Exp. Therap. 1961, 133, 117) consisting in following the evolution of the temperature in control rats and in treated rats, for 4 hours, after the subcutaneous administration of a pyrogen agent (containing bear yeast).

The activity is determined for oral, intraperitoneal, and intravenous route administrations at the doses indicated in the following table.

| Batches | Time | | | | | |
|---|---|---|---|---|---|---|
| | 0 | 30 mins. | 1 hr. | 2 hrs. | 3 hrs. | 4 hrs. |
| Pyrexia control | 39.1° C. | 39.3° C. | 39.1.° C. | 39° C. | 38.9° C. | 38.7° C. |
| Paracetamol 150 mg/kg (1 millimole) by oral route | 39.1° C. | 38.1° C. | 37.7° C. | 37° C. | 37° C. | 37.6° C. |
| Product of the invention (disodium salt) 275 mg/kg (1 millimole) by oral route | 39.2° C. | 38.2° C. | 37.5° C. | 36.8° C. | 37.3° C. | 38.3° C. |
| Disodium salt 275 mg/kg by intraperitoneal route | 39.2° C. | 38.3° C. | 37.6° C. | 37° C. | 36.9° C. | 38.1° C. |
| Disodium salt 100 mg/kg by intravenous route | 39° C. | 38.3° C. | 37.8° C. | 37.7° C. | 38.4° C. | — |

GLYCINE SALTS OF P-ACETAMINOPHENYL PHOSPHATE (PM 306)

(1) Analgesic activity (with mice)

By oral route, the active dose 50 (dose for which a 50% activity is obtained, or $DA_{50}$) is 520 ml/kg.

(2) Antipyretic activity (with rats)

The administered dose is 1 millimole, i.e. 306 mg/kg. The results obtained (temperature) are given in the following tables:

By oral route:

| Batches | Time | | | | | | |
|---|---|---|---|---|---|---|---|
| | 0 | 30 mins. | 1 hr. | 1h 30 mins. | 2 hrs. | 3 Hrs. | 4 hrs. |
| Absolute control | 37.6° C. | 38° C. | 37.9° C. | 38° C. | 38° C. | 37.4° C. | 37.2° C. |
| Pyrexia control | 38.8° C. | 39.1° C. | 39.2° C. | 39.2° C. | 39.1° C. | 38.9° C. | 38.8° C. |
| Glycine salt | 38.9° C. | 38.8° C. | 38° C. | 37.7° C. | 37.5° C. | 37.7° C. | 38.6° C. |

By intravenous route:

| Batches | Time | | | | | | |
|---|---|---|---|---|---|---|---|
| | 0 | 30 mins. | 1 hr. | 1h 30 mins. | 2 hrs. | 3 hrs. | 4 hrs. |
| Absolute control | 37.1° C. | 38.4° C. | 38.1° C. | 38° C. | 37.7° C. | 37.7° C. | 37.4° C. |
| Pyrexia control | 38.6° C. | 39.6° C. | 39.8° C. | 39.2° C. | 39.2° C. | 38.5° C. | 38.3° C. |
| Glycine salt | 38.8° C. | 38.6° C. | 37.8° C. | 37.5° C. | 37.2° C. | 38.1° C. | 39.0° C. |

(3) Acute toxicity ($DL_{50}$) with mice

The $DL_{50}$, by oral route, is 1,850 mg/kg (6.04 millimoles/kg).

LYSINE SALT OF P-ACETAMINOPHENYL PHOSPHATE (1) Analgesic Activity (with mice)

The $DA_{50}$, by oral route, is 625 mg/kg.

(2) Antipyretic activity (with rats)

The administered dose was 377 mg/kg (1 millimole/kg)

The results are given in the tables hereunder.

By oral route:

| Batches | Time | | | | | | |
|---|---|---|---|---|---|---|---|
| | 0 | 30 mins. | 1 hr. | 1h 30 mins. | 2 hrs. | 3 hrs. | 4 hrs. |
| Absolute control | 37.6° C. | 38° C. | 37.9° C. | 38° C. | 38° C. | 37.4° C. | 37.2° C. |
| Pyrexia control | 38.8° C. | 39.1° C. | 39.2° C. | 39.2° C. | 39.1° C. | 38.9° C. | 38.8° C. |
| Lysine salt | 38.9° C. | 38.7° C. | 38° C. | 37.3° C. | 37.2° C. | 37.7° C. | 38° C. |

By intravenous route:

| Batches | Time | | | | | | |
|---|---|---|---|---|---|---|---|
| | 0 | 30 mins. | 1 hr. | 1h 30 mins. | 2 hrs. | 3 hrs. | 4 hrs. |
| Absolute control | 37.1° C. | 38.4° C. | 38.1° C. | 38° C. | 37.7° C. | 37.7° C. | 37.4° C. |
| Pyrexia control | 38.6° C. | 39.6° C. | 39.8° C. | 39.2° C. | 39.2° C. | 38.5° C. | 38.3° C. |
| Lysine salt | 38.8° C. | 38.6° C. | 37.8° C. | 37.5° C. | 37.2° C. | 38.1° C. | 39.0° C. |

(3) Acute toxicity ($DL_{50}$)(with mice)

By oral route the $DL_{50}$ is 1,875 mg/kg (4.97 millimoles/kg.

ADENOSINE SALT OF P-ACETAMINOPHENYL PHOSPHATE (1) Analgesic activity (with mice)

By oral route, the $DA_{50}$ is 920 mg/kg (2) Antipyretic activity (with rats)

The dose administered by oral route was 498 mg/kg, i.e. 1 millimole/kg.

The results are given in the following table;

| Batches | Time | | | | | | |
|---|---|---|---|---|---|---|---|
| | 0 | 30 mins. | 1 hr. | 1h 30 mins. | 2 hrs. | 3 hrs. | 4 hrs. |
| Absolute control | 37.6° C. | 38.0° C. | 38.0° C. | 38.0° C. | 38.1° C. | 37.2° C. | 37.3° C. |
| Pyrexia control | 38.9° C. | 39.2° C. | 39.0° C. | 38.8° C. | 38.7° C. | 38.8° C. | 38.9° C. |
| Adenosine salt | 39.0° C. | 37.7° C. | 36.9° C. | 36.7° C. | 36.8° C. | 37.6° C. | 38.3° C. |

(3) Absolute toxicity ($DL_{50}$) with mice

By oral route, the $DL_{50}$ is 2,620 mg/kg (5.26 millimoles/kg).

What is claimed is:

1. Para-acetaminophenyl phosphate of the formula

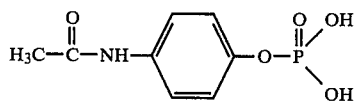

or a salt thereof with a pharmaceutically acceptable mineral or organic base.

2. A method of alleviating pain or hyperthermia in an animal comprising orally or parenterally administering a compound as defined by claim 1.

3. The method as defined by claim 2 wherein the compound is orally administered.

4. An analgesic or antipyretic therapeutic composition comprising a salt of p-acetaminophenyl phosphate with a pharmaceutically acceptable mineral or organic base.

5. The therapeutic composition of claim 4 in the form of a tablet or sachet for oral administration.

6. The therapeutic composition of claim 4 in the form of an injectable vial for intramuscular or intravenous administration.

7. The disodium salt of the para-acetaminophenyl phosphate of claim 1.

8. The glycine salt of the para-acetaminophenyl phosphate of claim 1.

9. The lysine salt of the para-acetaminophenyl phosphate of claim 1.

10. The adenosine salt of the para-acetaminophenyl phosphate of claim 1.

* * * * *